(12) United States Patent
Nemitz et al.

(10) Patent No.: US 12,070,517 B2
(45) Date of Patent: Aug. 27, 2024

(54) THICKENED ALKALYZATION COMPONENT FOR OXIDATIVE HAIR DYEING PRODUCT

(71) Applicant: Henkel AG & Co. KGaA, Duesseldorf (DE)

(72) Inventors: Oliver Nemitz, Duesseldorf (DE); Anja Reichert, Duesseldorf (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 59 days.

(21) Appl. No.: 18/002,030

(22) PCT Filed: Jun. 11, 2021

(86) PCT No.: PCT/EP2021/065813
§ 371 (c)(1),
(2) Date: Dec. 15, 2022

(87) PCT Pub. No.: WO2021/254909
PCT Pub. Date: Dec. 23, 2021

(65) Prior Publication Data
US 2023/0338267 A1    Oct. 26, 2023

(30) Foreign Application Priority Data

Jun. 17, 2020 (DE) .......... 102020207463.1

(51) Int. Cl.
*A61Q 5/10* (2006.01)
*A61K 8/73* (2006.01)

(52) U.S. Cl.
CPC ............ *A61K 8/731* (2013.01); *A61Q 5/10* (2013.01); *A61K 2800/4322* (2013.01); *A61K 2800/87* (2013.01)

(58) Field of Classification Search
CPC ............ A61K 8/731; A61K 2800/4322; A61K 2800/87; A61K 2800/882; A61K 8/41; A61Q 5/10
USPC ............................................. 8/405
See application file for complete search history.

(56) References Cited

U.S. PATENT DOCUMENTS

| | | | |
|---|---|---|---|
| 2005/0008593 A1* | 1/2005 | Plos | A61K 8/8158 424/63 |
| 2006/0117494 A1* | 6/2006 | Marsh | A61K 8/416 8/405 |
| 2007/0186357 A1* | 8/2007 | Chalmers | A61K 8/19 8/405 |

FOREIGN PATENT DOCUMENTS

| | | |
|---|---|---|
| WO | 2015028015 A1 | 3/2015 |
| WO | 2017008949 A1 | 1/2017 |
| WO | 2020064270 A1 | 4/2020 |

* cited by examiner

*Primary Examiner* — Eisa B Elhilo
(74) *Attorney, Agent, or Firm* — Lorenz & Kopf, LLP

(57) ABSTRACT

The present invention relates to a water-based cosmetic composition thickened with xanthan gum and sodium carboxymethyl cellulose and having a strongly alkaline pH. to be used as an alkalizing component in a two-part oxidative hair dye.

19 Claims, No Drawings

THICKENED ALKALYZATION COMPONENT FOR OXIDATIVE HAIR DYEING PRODUCT

CROSS-REFERENCE TO RELATED APPLICATION

This application is a U.S. National-Stage entry under 35 U.S.C. § 371 based on International Application No. PCT/EP2021/065813, filed Jun. 11, 2021, which was published under PCT Article 21(2) and which claims priority to German Application No. 102020207463.1, filed Jun. 17, 2020, which are all hereby incorporated in their entirety by reference.

TECHNICAL FIELD

The present disclosure relates to a water-based cosmetic composition thickened with xanthan gum and sodium carboxymethyl cellulose, having a strongly alkaline pH, to be used as an alkalizing component in a two-part oxidative hair colorant. The present disclosure also relates to a kit comprising said alkalizing component and to a hair dyeing method using said alkalizing component.

BACKGROUND

Changing one's own hair color, but also covering already graving hair with a dye in the tone of one's original hair color, is a desire of many consumers.

Changing the color of keratin fibers, especially hair, is an important area of modern cosmetics. As a result, the appearance of the hair can be adapted both to current fashion trends and to the individual wishes of the individual person. The expert knows different possibilities for changing the hair color. The hair color can be changed temporarily by using direct dye. Here, already fully formed dyes from the dye diffuse into the hair fiber. Dyeing with direct dyes is associated with low hair damage. A disadvantage, however, is the low durability and rapid washout of dyeing obtained with direct-pull dyes.

If the consumer desires a long-lasting color result or a shade lighter than his or her original hair color, oxidative color modifiers, known as oxidation dyes, are commonly used. Oxidation dyes provide long-lasting, intense coloration with high fastness properties. They contain oxidation dye precursors (OFV), which are divided into so-called developer components (oxidation bases) and coupler components. The oxidation dye precursors form the actual dyes under the influence of oxidizing agents together. Developer components can also form dyes without the presence of couplers under the influence of oxidizing agents, such as hydrogen peroxide. Coupler components alone do not form dyes under the influence of oxidizing agents, such as hydrogen peroxide, but they do react with the developer components. A wide range of color shades can be covered by clever selection of developer/coupler blends.

The application of an oxidizing agent, such as hydrogen peroxide, inevitably also lightens the treated hair. Thus, the hair can also, to a limited extent, be dyed in shades which are lighter than the starting hair color of the hair. By employing the oxidizing agent, such as in particular hydrogen peroxide, the natural dyes which are responsible for the natural color of the hair, in particular the endogenous melanins eumelanin and pheomelanin, are oxidatively degraded and the natural hair color is thus decolorized and lightened.

In order for the oxidant to perform optimally, oxidative colorants require an alkaline pH to accelerate the reaction, particularly in the range of pH 10.0 to 11.0. However, hydrogen peroxide, the oxidizing agent most commonly used for cosmetic purposes, can only be stored at low pH values, i.e. in the range of pH 2.0 to 6.5. Therefore, commercially available oxidation dyes are usually prepared as a kit comprising an aqueous hydrogen peroxide solution with a more acidic pH, preferably in the range of pH 2.0 to 6.5, and a dye-containing alkalizing component. Both components are only mixed together shortly before application to the hair. The composition and mixing ratio of the two components are matched to one another in such a way that the resulting application mixture has an alkaline pH value, in particular in the range of pH 9 to 10. Often, the kits described above still contain one or more portions of a hair conditioner for the nourishing after-treatment of the hair after the color treatment has taken place.

The application time for appealing coloring results is usually in the range of 5 to 60 minutes. It is therefore necessary that the individual components of the ready-to-use colorant are formulated in such a way that, on the one hand, they are readily mixable with each other and then distributable on the hair to be colored, and, on the other hand, they are sufficiently viscous to remain on the hair to be colored during the application time without dripping down. his viscosity can be adjusted by polymeric thickeners, it being possible for this thickener to be present both in the alkalizing component and in the oxidizing agent preparation.

The alkaline pH of the alkalizing component is adjusted with alkalizing agents, mainly ammonium hydroxide or ammonia water or alkanolamines as well as mixtures of these alkalizing agents. Ammonium hydroxide and alkanolamines, especially monoethanolamine, are particularly good at swelling the cuticle, i.e. the outer cuticle layer of the keratin fiber, so that the OFV and the oxidizing agent can penetrate well into the keratin fiber. Basic amino acids and inorganic bases are less suitable as sole alkalizing agents: however, these components can be used as additional alkalizing agents.

To prepare the ready-to-use colorant, the alkalizing component is usually mixed with an aqueous hydrogen peroxide solution to form a homogeneous cream or gel and then applied directly to the hair to be colored. This ready-to-use dye remains on the hair for a period of 5 to 60 minutes until the coloring is completed to the desired extent. Then the dye is washed out of the hair. The color result obtained depends on various properties of the hair, in particular on the structure of the hair fibers, in addition to the original amount of the black-brown pigment eumelanin and the red-gold pigment phaeomelanin. A good colorant is capable of achieving the most uniform possible color result along the keratin fiber, which is independent of the degree of damage to the keratin fiber along its length. On the more damaged hair lengths and ends, the OFV and oxidant can penetrate faster and better than on the hair near the hairline or root. On the less damaged hair near the hairline or root, the same shade should be achieved as possible as on the more damaged hair tip. This property of the colorant is also called leveling capacity.

The oxidation dye precursors (OFVs) and the alkalizing agent or alkalizing agent mixture are usually incorporated into a cosmetically suitable carrier, such as a cream or gel. The carrier ensures a homogeneous distribution and a sufficient residence time of the hair dye on the hair. The dye-containing alkalizing component of an oxidative hair dye is often also referred to as dye cream. Fat components with a melting point above 30° C. often serve as consistency agents for creams. These include in particular higher linear fatty alcohols, such as myristyl alcohol, cetyl alcohol and stearyl alcohol, and polyol esters, such as glyceryl monostearate, glyceryl distearate, ethylene glycol monostearate and ethylene glycol distearate, but also wax esters, such as cetyl palmitate and myristyl myristate, and hydrogenated oils, e.g. hydrogenated castor oil.

A disadvantage is the complex production of such a cream, which comprises higher-melting consistency agents. A lot of energy is required to melt the fat components and emulsify them with the water phase. The subsequent cooling process consumes large amounts of cooling water.

Instead of or in addition to higher-melting fat-based consistency agents, thickening can also be achieved by employing a polymer thickener. Corresponding alkalizing components as per the state of the art contain for this purpose polymers or copolymers with acrylate-, methacrylate- or vinyl-containing monomers, e.g. carbomer, sodium polyacrylates, PVP, amphiphilic polyacrylate copolymers, such as copolymers with the INCI designations Acrylates/C10-30 Alkyl Acrylate Cross polymer and Acrylates/Steareth-20 Methacrylate Copolymer, or polyurethanes, e.g. PEG-150/Decyl Alcohol/SMDI Copolymer. Such polymers and copolymers are hydrophilic or amphiphilic and form a gel skeleton in the alkaline aqueous phase. Due to their persistence in the environment, the use of such polymers should be avoided wherever possible. Products with such ingredients are classified in water hazard class 2 (WGK 2), i.e. as "clearly hazardous to water".

Another disadvantage of alkalizing components thickened with a vinyl, acrylate or polyurethane polymer is that the texture of the gels can sometimes have a detrimental effect on the spread ability of the product on the hair.

BRIEF SUMMARY

This disclosure provides an alkalizing component for an oxidative hair dyeing composition comprising
- about 76-about 92 wt. % water,
- about 1-about 2 wt. % xanthan gum,
- about 0.5-about 1.5 wt. % sodium carboxymethyl cellulose,
- at least one dye selected from oxidation dye precursors and direct dyes and mixtures thereof in a total amount of about 0.0001-about 6 wt. %,
- at least one alkalizing agent selected from ammonium hydroxide and alkanolamines and mixtures thereof in a total amount of about 3-about 9 wt. %,
- at least one oil in a total amount of about 0.5-about 7.0 wt. %,
- at least one surfactant chosen from anionic, zwitterionic, amphoteric and alkyl oligoglycoside surfactants substituted with at least one C8 to C14 alkyl radical, in a total amount of about 0.4-about 2 wt. %,
- about 0-about 0.1 wt. % peroxide,
- where all figures in % by weight are based on the weight of the alkalizing component,
- wherein the alkalizing component has a pH in the range of about 8.0 to about 12.0, measured at about 20° ° C.,
- where no percarbonate is present,
- wherein no polymer or copolymer with acrylate-, methacrylate- or vinyl-containing monomers and no polyurethane is present, and wherein no fat component having a melting point of about 28° C. or higher is included.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It is to be appreciated that all numerical values as provided herein, save for the actual examples, are approximate values with endpoints or particular values intended to be read as "about" or "approximately" the value as recited.

Consequently, the present disclosure was based on the tasks of providing a thickened alkalizing component for an oxidative hair dyeing composition, which
- leads to improved dyeing results, especially with regard to the amount of oxidant required,
- the uniformity of the coloring along the keratin fiber (leveling), and
- the absence of an undesirable yellow cast,
- is more environmentally friendly in the production as well as in the selection of ingredients,
- is easier to distribute on the hair.

These tasks are solved by an alkalizing component for an oxidative hair dyeing composition containing
- 76-92 wt. % water,
- 1-2 wt. % xanthan gum,
- 0.5-1.5 wt. % sodium carboxymethyl cellulose,
- at least one dye selected from oxidation dye precursors and direct dyes and mixtures thereof, in a total amount of 0.0001-6 wt. %,
- at least one alkalizing agent selected from ammonium hydroxide and alkanolamines and mixtures thereof, in a total amount of 3-9 wt. %,
- at least one oil in a total amount of 0.5-7.0 wt. %, preferably 2.0 to 5.5 wt. %, more preferably 3.5 to 5.0 wt. %,
- at least one surfactant selected from anionic, zwitterionic, amphoteric and alkyl oligoglycoside surfactants substituted with at least one C8 to C14 alkyl radical, in a total amount of 0.4-2 wt. %,
- 0-0.1 wt. % peroxide,
- where all figures in % by weight are based on the weight of the alkalizing component,
- wherein the alkalizing component has a pH in the range of 8.0 to 12.0, preferably in the range of 9.6 to 11.5, particularly preferably in the range of 10.0 to 11.0, measured at 20° C.,
- where no percarbonate is present,
- wherein no polymer or copolymer with acrylate-, methacrylate- or vinyl-containing monomers and no polyurethane is present, and
- wherein no fat component having a melting point of 28° C. or higher is included.

The alkalizing component as contemplated herein comprises, in each case based on its weight, water in an amount of 76-92 wt. %, preferably 80-89 wt. %, particularly preferably 82-86 wt. %.

The alkalizing component as contemplated herein comprises, in each case based on its weight, xanthan gum in an amount of 1-2 wt. %, preferably 1.2-1.8 wt. %, particularly preferably 1.5-1.7 wt. %.

The alkalizing component as contemplated herein comprises, in each case based on its weight, sodium carboxymethylcellulose in an amount of 0.5-1.5 wt. %, preferably 0.7-1.1 wt. %, particularly preferably 0.8-0.9 wt. %.

Alkalizing components preferred as contemplated herein are exemplified by the fact that, apart from xanthan gum and sodium carboxymethyl cellulose, no other polysaccharide is present.

The alkalizing components as contemplated herein are further exemplified in that at least one dye selected from oxidation dye precursors and direct dyes and mixtures thereof is present in a total amount of 0.0001-6% by weight, based on the weight of the alkalizing component.

Alkalizing components preferred as contemplated herein are exemplified in that at least one oxidation dye precursor selected from developer components and coupler components and mixtures thereof is included, wherein at least one developer component is included.

Developer components preferred as contemplated herein are selected from the group formed by toluene-2,5-diamine, 2-methoxymethyl-p-phenylenediamine, 2-(2.5-diaminophenyl)ethanol, p-phenylenediamine, 2-(1.2-dihydroxyethyl)-p-phenylenediamine, N,N-bis-(2-hydroxyethyl)-p-phenylenediamine, 4.5-diamino-1-(2-hydroxyethyl)-1H-pyrazole, 4-aminophenol, 3-methyl-4-aminophenol, N-(4-amino-3-methylphenyl)-N-[3-(1H-imidazol-1-yl)propyl]amine, N,N'-bis-(2-hydroxyethyl)-N, N'-bis-(4-aminophenyl)-1,3-diamino-propan-2-ol, bis-(2-hydroxy-5-aminophenyl)methane, 1.3-bis-(2.5-diaminophenoxy)propan-2-ol, N,N'-bis-(4-aminophenyl)-1.4-diazacycloheptane, 1,10-bis-(2,5-diaminophenyl)-1,4,7,10-tetraoxadecane, 2, 4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo-[1,2-a]-pyrazol-1-one and physiologically tolerated salts and mixtures thereof.

Preferred physiologically acceptable salts of the oxidation dye precursors having one or more amine groups are in particular the hydrochlorides (monohydrochloride×HCl, or dihydrochloride×2 HCl), the sulfate (×H$_2$SO$_4$), and the hydrobromides (monohydrobromide×HBr, or dihydrobromide×2 HBr) of the compound.

Alkalizing components preferred as contemplated herein are exemplified in that at least one developer component selected from toluene-2.5-diamine, 2-methoxymethyl-p-phenylenediamine, 2-(2,5-diaminophenyl)ethanol, p-phenylenediamine, 2-(1, 2-dihydroxyethyl)-p-phenylenediamine, N,N-bis-(2-hydroxyethyl)-p-phenylenediamine, 4,5-diamino-1-(2-hydroxyethyl)-1H-pyrazole, 4-aminophenol, 3-methyl-4-aminophenol, N-(4-amino-3-methylphenyl)-N-[3-(1H-imidazol-1-yl)propyl]amine, N,N'-bis-(2-hydroxyethyl)-N, N'-bis-(4-aminophenyl)-1,3-diamino-propan-2-ol, bis-(2-hydroxy-5-aminophenyl)methane, 1,3-bis-(2,5-diaminophenoxy)propan-2-ol, N, N'-bis-(4-aminophenyl)-1,4-diazacycloheptane, 1,10-bis-(2,5-diaminophenyl)-1,4,7,10-tetraoxadecane, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo-[1,2-a]-pyrazol-1-one and physiologically acceptable salts and mixtures thereof, in a total amount of 0.0001-6 wt.-%, preferably 0.01-4 wt. %, particularly preferably 0.05-3 wt. %, in each case based on the weight of the alkalizing component.

Alkalizing components preferred as contemplated herein are exemplified in that at least one oxidation dye precursor selected from developer components and coupler components and mixtures thereof is included, wherein at least one developer component, selected from toluene-2.5-diamine, 2-methoxymethyl-p-phenylenediamine, 2-(2.5-diaminophenyl)ethanol, p-phenylenediamine, 2-(1,2-dihydroxyethyl)-p-phenylenediamine, N,N-bis-(2-hydroxyethyl)-p-phenylenediamine, 4,5-diamino-1-(2-hydroxyethyl)-1H-pyrazole, 4-aminophenol, 3-methyl-4-aminophenol, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diamino-propan-2-ol, Bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1, 4,7,10-tetraoxadecane, 2.4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo-[1,2-a]-pyrazol-1-one and physiologically tolerated salts and mixtures thereof, in a total amount of 0.0001-6 wt.-%, preferably 0.01-4 wt. %, particularly preferably 0.05-3 wt. %, in each case based on the weight of the alkalizing component.

Further alkalizing components preferred as contemplated herein are exemplified in that, in addition to at least one developer component, at least one coupler component is further included. Coupler components alone do not form a significant coloration in the course of oxidative dyeing, but always require the presence of developer components. Coupler components as contemplated herein allow at least one substitution of a chemical residue of the coupler by the oxidized form of the developer component. In the process, covalent bonds are formed between the coupler and developer components. As a coupler component suitable as contemplated herein, at least one compound is preferably selected from one of the following classes:

m-Aminophenol and/or derivatives thereof,
m-dihydroxybenzene and/or derivatives thereof,
m-diaminobenzene and/or derivatives thereof,
o-Diaminobenzene and/or derivatives thereof,
o-aminophenol derivatives, such as o-aminophenol,
Naphthalene derivatives having at least one hydroxy group,
Di- or trihydroxybenzene, respectively, and/or derivatives thereof,
Pyridine derivatives,
Pyrimidine derivatives,
Monohydroxyindole derivatives and/or monoaminoindole derivatives,
Monohydroxyindoline derivatives and/or monoaminoindoline derivatives,
Pyrazolone derivatives, such as 1-phenyl-3-methylpyrazol-5-one,
Morpholine derivatives, such as 6-hydroxy benzomorpholine or 6-aminobenzomorpholine,
Quinoxaline derivatives, such as 6-methyl-1,2,3,4-tetrahydroquinoxaline.

Mixtures of two or more compounds from one or more of these classes are also contemplated herein in the context of this embodiment.

Further alkalizing components preferred as contemplated herein are exemplified in that, in addition to at least one developer component, at least one coupler component is further included which is selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino) ethanol, 2-({3-[(2-hydroxyethyl)amino]-2-methoxy-5- methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, Resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3, 5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline and/or 7-hydroxyindoline and physiologically tolerated salts thereof, as well as mixtures of the aforementioned substances.

Further alkalizing components preferred as contemplated herein are exemplified in that, in addition to at least one developer component, at least one coupler component is further present in a total amount of 0.001-5.5 wt. %, preferably 0.05-4 wt. %, particularly preferably 0.2-3 wt. %. %, in each case based on the weight of the alkalizing component, the coupler component being selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxy benzene, 2-amino-3-dimethylpyridine, 3,5-diamino-2, 6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline and/or 7-hydroxyindoline and physiologically tolerated salts thereof, as well as mixtures of the aforementioned substances.

In principle, it is also possible that the alkalizing component as contemplated herein does not contain an oxidation dye precursor, but only at least one direct-drawing dye, abbreviated as direct-drawing dye. In addition, it may be preferred that alkalizing components preferred as contemplated herein contain at least one oxidation dye precursor and further at least one direct dye.

The direct dyes suitable as contemplated herein are selected from the group of anionic, nonionic and/or cationic direct dyes.

In a further particularly preferred embodiment, an alkalizing component as contemplated herein is exemplified in that it comprises at least one direct dye in a total amount of 0.0001-6 wt. %, preferably 0.001-4 wt. %, particularly preferably 0.05-3 wt. %, in each case based on the weight of the alkalizing component.

Particularly preferred are one or more nonionic direct dyes from the group, HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, 1,4-diamino-2-nitrobenzene, 2-amino-4-nitrophenol, 1,4-bis(2-hydroxyethyl)amino-2-nitrobenzene, 3-nitro-4-(2-hydroxy ethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxy propyl)amino]-3-nitrophenol, 4-nitro-o-phenylenediamine, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitrophenol.

A further particularly preferred embodiment, an alkalizing component as contemplated herein is exemplified in that it comprises one or more nonionic direct dyes selected from the group of HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, 1,4-diamino-2-nitrobenzene, 2-amino-4-nitrophenol, 1,4-bis-(2-hydroxyethyl)-amino-2-nitrobenzene, 3-nitro-4-(2-hydroxy ethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitrophenol.

Another particularly preferred embodiment, an alkalizing component as contemplated herein is exemplified in that it comprises one or more anionic direct dyes selected from the group of Acid Yellow 1, Yellow 10, Acid Yellow 23, Acid Yellow 36, Acid Orange 7, Acid Red 33, Acid Red 52, Pigment Red 57: 1, Acid Blue 7, Acid Green 50, Acid Violet 43, Acid Black 1, Acid Black 52, Bromophenol Blue and Tetrabromophenol Blue, preferably in a total amount of 0.0001-3% wt.-%, preferably 0.001-2 wt. %, particularly preferably 0.05-1 wt. %, in each case based on the weight of the alkalizing component.

Suitable cationic direct dyes are cationic triphenylmethane dyes, such as Basic Blue 7, Basic Blue 26, Basic Violet 2 and Basic Violet 14, aromatic systems substituted with a quaternary nitrogen group, such as Basic Yellow 57, Basic Red 76, Basic Blue 99, Basic Brown 16 and Basic Brown 17, cationic anthraquinone dyes, such as HC Blue 16 (Bluequat B), and direct dyes containing a heterocycle having at least one quaternary nitrogen atom, in particular Basic Yellow 87, Basic Orange 31 and Basic Red 51.

In another particularly preferred embodiment, an alkalizing component as contemplated herein is exemplified in that it comprises one or more cationic direct dyes selected from the group of Basic Blue 7, Basic Blue 26, Basic Violet 2, Basic Violet 14, Basic Yellow 57, Basic Red 76, Basic Blue 99, Basic Brown 16, Basic Brown 17, HC Blue 16 (Bluequat B) Basic Yellow 87, Basic Orange 31 and Basic Red 51.

A further particularly preferred embodiment, an alkalizing component as contemplated herein is exemplified in that it comprises one or more cationic direct dyes from the group comprising Basic Blue 7, Basic Blue 26, Basic Violet 2, Basic Violet 14, Basic Yellow 57, Basic Red 76, Basic Blue 99, Basic Brown 16, Basic Brown 17, HC Blue 16 (Bluequat B) Basic Yellow 87, Basic Orange 31 and Basic Red 51 in a total amount of 0.0001-3 wt. %, preferably 0.001-2 wt. %, particularly preferably 0.05-1 wt. %, in each case based on the weight of the alkalizing component. %, preferably 0.001-2 wt. %, particularly preferably 0.05-1 wt. %, in each case based on the weight of the alkalizing component.

The alkalizing component as contemplated herein comprises, in each case based on its weight, at least one alkalizing agent selected from ammonium hydroxide and alkanolamines and mixtures thereof, in a total amount of 2-9 wt. %, preferably in a total amount of 3-8 wt. %, particularly preferably in a total amount of 4-7.5 wt. %.

Alkalizing components preferred as contemplated herein contain, in each case based on their weight, 3-5 wt. %, preferably 3.5-4 wt. % ammonium hydroxide.

Alkanolamines which can be used as alkalizing agents as contemplated herein are preferably selected from primary amines having a $C_2$-$C_6$ alkyl parent carrying at least one hydroxyl group. Particularly preferred alkanolamines are selected from the group formed by 2-aminoethan-1-ol 3-aminopropan-1-ol, (monoethanolamine), 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, and mixtures thereof. Alkanolamines which are very particularly preferred as contemplated herein are selected from the group of 2-aminoethan-1-ol, 2-amino-2-methylpropan-1-ol and 2-amino-2-methylpropane-1,3-diol and mixtures thereof. An exceptionally preferred alkanolamine as contemplated herein is 2-aminoethan-1-ol (monoethanolamine).

Alkalizing components preferred as contemplated herein contain at least one alkanolamine selected from primary amines having a $C_2$-$C_6$ alkyl parent carrying at least one hydroxyl group in a total amount of 2-9 wt. %, preferably 3-8 wt. %, particularly preferably in a total amount of 4-7.5 wt. %, in each case based on their weight.

Further alkalizing components preferred as contemplated herein contain at least one alkanolamine selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, and mixtures thereof, in a total amount of 2-9 wt.-%, preferably 3-8 wt. %, particularly preferably in a total amount of 4-7.5 wt. %, in each case based on their weight.

Further alkalizing components preferred as contemplated herein contain, in each case based on their weight, 2-9 wt. %, preferably 3-8 wt. %, particularly preferably 4-7.5 wt. % 2-aminoethan-1-ol (monoethanolamine).

The choice of alkalizing agent depends, among other things, on the desired degree of color intensity and whether a dark or light coloration is to be achieved. Particularly preferred is a mixture of ammonium hydroxide and at least one alkanolamine selected as alkalizing agent in a total amount of 4-9 wt. %, preferably of 5-8 wt. %, particularly preferably of 6 to 7 wt. %, in each case based on the weight of the alkalizing component. A mixture of ammonium hydroxide and 2-aminoethan-1-ol (monoethanolamine) in a total amount of 4-9 wt. %, preferably 5-8 wt. %, particularly preferably 6-7 wt. %, in each case based on the weight of the alkalizing component, is preferred.

Furthermore, the alkalizing component as contemplated herein comprises, in each case based on its weight, at least one oil in a total amount of 0.5-7.0 wt. %, preferably 2.0 to 5.5 wt. %, particularly preferably 3.5 to 5.0 wt. %. The addition of an oil in the specified amounts supports the leveling capacity of the colorant, i.e. ensures a uniform color result, regardless of the degree of damage along the keratin fiber. In addition, the oil optimizes the texture of the alkalizing component of the present disclosure.

Alkalizing components preferred as contemplated herein are exemplified in that the at least one oil is selected from branched, saturated fatty alcohols having 6-30 carbon atoms and from the esters of saturated, linear or branched fatty alcohols having 2-30 carbon atoms with saturated, linear or branched fatty acids having 2-30 carbon atoms, which may be hydroxylated, and mixtures thereof.

The branched alcohols are often referred to as Guerbet alcohols because they are available after the Guerbet reaction. Preferred branched, saturated fatty alcohols with 6-30 carbon atoms are 2-hexyldecanol, 2-octyldodecanol, 2-ethylhexyl alcohol and isostearyl alcohol, and mixtures thereof. Exceptionally preferred is 2-octyldodecanol. Other oils particularly preferred as contemplated herein are selected from the esters of saturated, linear or branched fatty alcohols having 2-30 carbon atoms with saturated, linear or branched fatty acids having 2-30 carbon atoms, which may be hydroxylated. These preferably include cetyl 2-ethylhexanoate, 2-hexyldecyl stearate, 2-hexyldecyl laurate, isodecyl neopentanoate, isononyl isononanoate, 2-ethylhexyl palmitate, 2-ethylhexyl stearate, isopropyl myristate, isopropyl palmitate, isopropyl stearate, isopropyl isostearate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyl dodecyl palmitate, butyloctanoic acid 2-butyloctanoate, diisotridecyl acetate, n-butyl stearate and n-hexyl laurate, and mixtures thereof.

Alkalizing components which are particularly preferred as contemplated herein are exemplified in that the at least one oil is selected from 2-hexyldecanol, 2-octyldodecanol, 2-ethylhexyl alcohol, isostearyl alcohol, cetyl 2-ethylhexanoate, 2-hexyldecyl stearate, 2-hexyldecyl laurate, isodecyl neopentanoate, isononyl isononanoate, 2-ethylhexyl palmitate, 2-ethylhexyl stearate, isopropyl myristate, isopropyl palmitate, isopropyl stearate, isopropyl isostearate, isooctyl stearate, isononyl stearate, isocetyl stearate, isononyl isononanoate, isotridecyl isononanoate, cetearyl isononanoate, 2-ethylhexyl laurate-, 2-ethylhexyl isostearate, 2-ethylhexyl cocoate, 2-octyldodecyl palmitate, butyloctanoic acid 2-butyloctanoate, diisotridecyl acetate, n-butyl stearate and n-hexyl-laurate, and mixtures thereof. Extremely preferred alkalizing components as contemplated herein are exemplified in that they contain, by weight, 0.5-7.0 wt. %, preferably 2.0 to 5.5 wt. %, particularly preferably 3.5 to 5.0 wt. %, of 2-octyldodecanol.

Furthermore, the alkalizing component as contemplated herein comprises, in each case based on its weight, at least one surfactant selected from anionic, zwitterionic, amphoteric and alkyl oligoglycoside surfactants substituted with at least one C8 to C14 alkyl radical, in a total amount of 0.4-2 wt. %, preferably 0.7-1.3 wt. %. Such a surfactant is required, on the one hand, to emulsify the at least one oil in a storage-stable manner and, on the other hand, to facilitate the washing of the hair colorant out of the hair.

Anionic Surfactant

Suitable anionic surfactants are all anionic surface-active substances suitable for use on the human body which have a water-solubilizing anionic group, for example a carboxylate, sulfate, sulfonate or phosphate group, and a lipophilic alkyl group with 8 to 14 C atoms, preferably 8 to 12 C atoms, in the molecule. In addition, glycol or polyglycol ether groups, ester, ether and amide and hydroxyl groups may also be present in the molecule. Examples of suitable anionic surfactants are, in each case in the form of the sodium, potassium and ammonium as well as the mono, di and trialkanolammonium salts with 2 to 4 C atoms in the alkanol group, linear and branched fatty acids with 8 to 14 C atoms (soaps), polyethoxylated ether carboxylic acids, acyl sarcosides, acyl taurides, acyl isethionates, sulfosuccinic acid mono- and dialkyl esters and sulfosuccinic acid mono-alkyl polyoxyethyl esters containing 1 to 6 ethylene oxide groups, linear alkane sulfonates, linear alpha-olefin sulfonates, sulfonates of unsaturated fatty acids with up to 6 double bonds, alpha-sulfofatty acid methyl esters of fatty acids, $C_8$-$C_{14}$ alkyl sulfates and $C_8$-$C_{14}$ alkyl ether sulfates with up to 15 oxyethyl groups, mixtures of surface-active hydroxysulfonates, sulfated hydroxyalkyl polyethylene and/or hydroxyalkylene propylene glycol ethers, esters of tartaric acid or citric acid with ethoxylated or propoxylated fatty alcohols, optionally polyethoxylated alkyl and/or alkenyl ether phosphates, sulfated fatty acid alkylene glycol esters, and monoglyceride sulfates and monoglyceride ether sulfates. Preferred anionic surfactants are $C_8$-$C_{14}$ alkyl sulfates, $C_8$-$C_{14}$ alkyl ether sulfates and $C_8$-$C_{14}$ ether carboxylic acids with 8 to 14 C atoms in the alkyl group and up to 12 ethylene oxide groups in the molecule. Preferred alkalizing components contain, by weight, at least one anionic surfactant in a total amount of 0.4-2 wt. %, preferably 0.7-1.3 wt. %. Sodium laureth(2) sulfate is particularly preferred. Exceptionally preferably, based on the weight of the alkalizing component, 0.4-2 wt. %, preferably 0.7-1.3 wt. Sodium laureth(2)sulfate is present.

Zwitterionic Surfactant

The term zwitterionic surfactants is used to describe surface-active compounds which, in addition to at least one lipophilic alkyl group containing 8 to 14 carbon atoms, preferably 8 to 12 carbon atoms, carry in the molecule at least one quaternary ammonium group and at least one carboxylate, sulfonate or sulfate group. Particularly suitable zwitterionic surfactants are the so-called betaines such as the N-alkyl-N,N-dimethylammonium glycinates, for example cocoalkyl dimethylammonium glycinate, N-acyl-aminopropyl-N,N-dimethylammonium glycinate, for example cocoacylaminopropyl dimethylammonium glycinate, and 2-alkyl-3-carboxymethyl-3-hydroxyethyl imidazolines each having 8 to 18 carbon atoms in the alkyl or acyl group, and cocoacylaminoethyl hydroxyethyl carboxymethyl glycinate. A preferred zwitterionic surfactant is the fatty acid amide derivative known under the INCI designation cocamidopropyl betaine. Preferred alkalizing components contain, by weight, at least one zwitterionic surfactant in a total amount of 0.4-2 wt. %, preferably 0.7-1.3 wt. %.

Amphoteric Surfactant

Amphoteric surfactants are surface-active compounds which, apart from a $C_8$-$C_{14}$ alkyl or acyl group, contain at least one free amino group and at least one —COOH or —SO$_3$H group in the molecule and are capable of forming internal salts. Examples of suitable amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having about 8 to 24 carbon atoms in the alkyl group. Particularly preferred amphoteric surfactants are N-Cocoalkylaminopropionate, Cocoacylaminoethylaminopropionate and $C_{12}$-$C_{18}$ Acylsarcosine. Preferred alkalizing components contain, by weight, at least one amphoteric surfactant in a total amount of 0.4-2 wt. %, preferably 0.7-1.3 wt. %.

Alkyl Oligoglycoside Surfactant

Other preferred surfactants are selected from $C_8$-$C_{14}$ alkyl oligoglycosides. $C_8$-$C_{14}$ alkyl oligoglycosides represent well-known, commercially available surfactants. They are produced in particular by reacting glucose or oligosaccharides with primary alcohols containing 8-14 carbon atoms. With regard to the glycoside residue, monoglycosides in which a cyclic sugar residue is glycosidically bonded to the fatty alcohol as well as oligomeric glycosides with a degree of oligomerization of up to about 8, preferably 1-2, are suitable. The degree of oligomerization is a statistical mean value based on a homologue distribution that is common for such technical products. Products available under the trademark Plantacare® contain a glucosidically bonded $C_8$-$C_{14}$ alkyl group on an oligoglucoside residue whose average degree of oligomerization is 1-2, in particular 1.2-1.4. Particularly preferred $C_8$-$C_{14}$ alkyl oligoglycosides are selected from octyl glucoside, decyl glucoside and lauryl glucoside, and mixtures thereof. Preferred alkalizing components contain, by weight, at least one $C_8$-$C_{14}$ alkyl oligoglycoside in a total amount of 0.4-2 wt. %, preferably 0.7-1.3 wt. %. As contemplated herein, alkyl oligoglycoside surfactants are not considered polysaccharides.

The obligatory feature "0-0.1 wt. % peroxide" is intended to express that the alkalizing component as contemplated herein is the peroxide-free component of an oxidative hair colorant prior to the production of the hair colorant ready for use. Small amounts of peroxide, which could be introduced by appropriate pretreatment of the water used for production, are considered acceptable. A peroxide content of up to 0.1 wt. %, based on the weight of the alkalizing component, does not yet color or lighten the hair.

The alkalizing component as contemplated herein has a pH in the range from 8.0 to 12.0, preferably in the range from 9.6 to 11.5, particularly preferably in the range from 10.0 to 11.0, in each case measured at 20° C.

The alkalizing component as contemplated herein comprises no percarbonate, i.e., based on its weight, 0.0 wt. % percarbonate.

The alkalizing component as contemplated herein comprises no polymer or copolymer with acrylate-, methacrylate- or vinyl-containing monomers and no polyurethane, i.e., based on its weight, 0.0 wt. % of the aforementioned (co-)polymers.

The alkalizing component as contemplated herein does not contain any fatty component with a melting point of 28° C. or higher, in particular fatty components with a melting point in the range from 28° C. to 300° C. Examples of such fat components undesirable as contemplated herein are linear, saturated 1-alkanols with at least 14 carbon atoms, such as 1-tetradecanol (myristyl alcohol), 1-hexadecanol (cetyl alcohol), 1-octadecanol (stearyl alcohol) and 1-icosanol (arachyl alcohol), waxes, such as beeswax or kerosene wax, esters of glycerol, 1.2-propylene glycol or of ethylene glycol, such as glyceryl monostearate, glyceryl distearate, hydrogenated castor oil, propylene glycol distearate, ethylene glycol monostearate or ethylene glycol distearate.

Alkalizing components preferred as contemplated herein are exemplified by having a viscosity in the range from 2,000 to 110,000 mPa·s, preferably 40,000 to 100,000 mPa·s, particularly preferably 70,000 to 90,000 mPa·s, in each case measured at 20° C.

The parameters for the viscosity measurements are:
Device: Brookfield viscometer RDV-II+; temperature: 20° C.: spindle 5; shear rate: 4 revolutions per minute (4 RPM).

These viscosities are excellent for handling this agent itself (preparation, dosing to prepare the mixture with the oxidant preparation).

Surprisingly, it was found that the leveling properties of a colorant based on an alkalizing component preferred as contemplated herein could be further improved by the addition of glucoheptonic acid and/or at least one of its physiologically tolerated salts and/or lactones.

Alkalizing components preferred as contemplated herein are therefore exemplified in that glucoheptonic acid and/or at least one of its physiologically compatible salts and/or lactones is present, preferably in a total amount of 0.1 to 2 wt. %, particularly preferably in a total amount of 0.6 to 1.5 wt. %, exceptionally preferably in a total amount of 0.8 to 1.1 wt. %, in each case based on the weight of free glucoheptonic acid in relation to the weight of the alkalizing component.

Glucoheptonic acid (226.18 g/mol) is also known as d-glycero-d-gulo heptonic acid. Physiologically acceptable salts of glucoheptonic acid suitable in the context of the present disclosure include in particular the salts of alkali metals, alkaline earth metals and earth metals, in particular of lithium, sodium, potassium, magnesium and calcium, particularly preferably sodium and potassium, exceptionally preferably sodium. Sodium glucoheptonate (INCI: sodium gluceptate: 248 g/mol), which is extremely preferred as contemplated herein, is commercially available.

Lactones of glucoheptonic acid preferred as contemplated herein include the 1,4-lactone (melting point 151° C.) and the 1,5-lactone, with the 1,4-lactone being exceptionally preferred.

Alkalizing components preferred as contemplated herein are exemplified in that glucoheptonic acid and/or at least one of its physiologically compatible salts and/or lactones is/are present in a total amount of 0.1 to 2 wt. %, particularly preferably in a total amount of 0.6 to 1.5 wt. %, exceptionally preferably in a total amount of 0.8 to 1.1 wt. %, the amounts being based on the weight of free glucoheptonic acid in relation to the weight of the alkalizing component as contemplated herein.

Surprisingly, it was found that the hair-conditioning properties of a colorant based on an alkalizing component preferred as contemplated herein could be further improved by the addition of at least one aminated silicone.

In another preferred embodiment of the present disclosure, the alkalizing component as contemplated herein comprises at least one aminated silicone. Preferred aminated silicones are selected from compounds of structural formula (I),

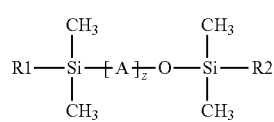

(I)

with

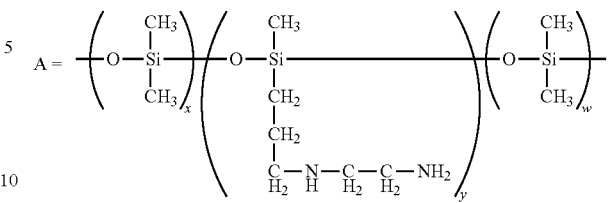

wherein
i. x and y stand independently for numbers from 1 to 100,
ii. w stands for a number from 0 to 100,
iii. z is a number from 1 to 100, whereby, if z≥is 2, the respective values x, y and w in a structural element A can each be selected independently of preceding structural elements A and
iv. R1 and R2 independently of one another represent a linear or branched, saturated, unsaturated or polyunsaturated $C_5$-$C_{20}$ alkyl group, a hydroxy group, a $C_1$-$C_{30}$ alkoxy group, a carboxy-$C_1$-$C_{30}$ alkyl group or a $C_1$-$C_6$ alkyl-(O—$CH_2$—$CH_2$)$_n$—O— group, wherein n is an integer from 1 to 60.

The structural elements A of the compound of the formula (I) are each composed of one or more elements 3-[(2-aminoethyl)amino]propyl-methyl-siloxane and one or more elements dimethylsiloxane. The number of dimethylsiloxane elements is defined by the parameter x. The number of 3-[(2-aminoethyl)amino]propyl-methyl-siloxane elements is defined by the parameter y. As contemplated herein, the values of the parameters x and y stand independently of each other for numbers between 1 and 100.

The number of structural elements A is defined by the parameter z. As contemplated herein, the value of the parameter z is between 1 and 100. If z≥2, the parameters x and y can be selected in each structural element A independently of preceding structural elements A. It follows that for case z≥2, the individual structural elements A may differ from one another in their number of 3-[(2-aminoethyl)amino]propyl-methyl-siloxane elements and/or in their number of dimethylsiloxane elements.

The siloxane structure of the compound(s) of formula (I) is terminated at both ends by the radicals R1 and R2, where R1 and R2, independently of one another, may represent a linear or branched, saturated, unsaturated or polyunsaturated $C_5$-$C_{20}$ alkyl chain, a hydroxyl group, a $C_1$-$C_{30}$ alkoxy group or a $C_1$-$C_6$ alkyl-(O—$CH_2$—$CH_2$)$_n$—O— group.

Another alkalizing component which is particularly preferred as contemplated herein is exemplified in that it comprises, by weight, at least one aminated silicone selected from compounds of the structural formula (I) in a total amount of 0.1 to 2 wt. %, particularly preferably in a total amount of 0.7 to 1.5 wt. %, exceptionally preferably in a total amount of 0.9 to 1.1 wt. %.

If R1 and/or R2 stand for a branched, saturated, unsaturated or polyunsaturated $C_5$-$C_{20}$ alkyl radical, the siloxane skeleton is terminated with a fatty alkyl chain. Fatty alkyl chains according to the present disclosure are all linear and/or branched, saturated and/or unsaturated and/or polyunsaturated carbon chains whose carbon chain is preferably a $C_6$-$C_{30}$ chain, particularly preferably a $C_8$-$C_{24}$ chain and particularly a $C_{14}$-$C_{20}$ chain. Examples of fatty alkyl chains as contemplated herein are hexyl, heptyl, octyl, nonyl, decyl, dodecyl, tetradecyl, pentadecyl, hexadecyl, heptadecyl, octadecyl, nonadecyl, eicosyl, docosyl, tetracosyl, hexacosyl, iso-stearyl, (9Z)-tetradeca-9-enyl, (9Z)-hexadeca-9-enyl, (6Z)-Octadeca-6-enyl, (9Z)-Octadeca-9-enyl, (9E)-Octadeca-9-enyl, (11E)-Octadeca-11-enyl, (9Z)-Eicosa-9-enyl, (11Z)-Eicosa-11-enyl, (11Z)-Docosa-11-enyl, (13Z)-Docosa-13-enyl, (15Z)-Tetracosa-15-enyl, (9Z,12Z)-Octadeca-9,12-dienyl, (9Z,12Z, 15Z)-Octadeca-9,12, 15-trienyl, (6Z,9Z,12Z)-Octadeca-6,9, 12-trienyl, (8E,10E, 12Z)-Octadeca-8,10,12-trienyl, (9Z,11E,13Z)-Octadeca-9, 11,13-trienyl, (9Z,11E,13E)-Octadeca-9,11, 13-trienyl, (9E, 11E, 13E)-Octadeca-9,11,13-trienyl, (5Z,8Z,11Z,14Z)-Eicosa-5,8, 11, 14-tetraenyl, (5Z,8Z, 11Z,14Z,17Z)-Eicosa-5, 8,11,14 17-pentaenyl, (7Z, 10Z, 13Z, 16Z,19Z)-Docosa-7, 10, 13,16, 19-pentaenyl, (4Z,7Z,10Z, 13Z,16Z, 19Z)-Docosa-4,7, 10, 13, 16, 19-hexaenyl. In a preferred embodiment of the present disclosure, the radicals R1 and R2 independently of one another represent linear alkyl chains, preferably $C_{14}$-$C_{20}$ alkyl, particularly preferably tetradecyl, pentadecyl, hexadecyl, heptadecyl, octadecyl, nonadecyl or eicosyl. Particularly preferred radicals R1 and/or R2 are hexadecyl (cetyl) and/or octadecyl (stearyl). Cetearyl is a mixture of cetyl and stearyl: this mixture is also preferred.

In a preferred embodiment, the alkalizing component as contemplated herein is therefore exemplified in that it comprises a compound of the formula (I) in which the substituents $R^1$ and $R^2$ independently of one another represent a linear or branched, saturated, unsaturated or polyunsaturated $C_5$-$C_{20}$-alkyl chain, preferably a linear $C_{14}$-$C_{20}$-alkyl chain, in particular preferably a member of the group $H_3C$—$(CH_2)_{13}$—, $H_3C$—$(CH_2)_{15}$—, $H_3C$—$(CH_2)_{17}$—, $H_3C$—$(CH_2)_{19}$—.

As contemplated herein, compounds of the formula (I) in which the radicals $R^1$ and $R^2$ independently of one another represent $H_3C$—$(CH_2)_{15}$— or $H_3C$—$(CH_2)_{17}$— are particularly preferred. In this case, the instant amodimethicone is a bis-tearyl amodimethicone.

In a further preferred embodiment, the alkalizing component as contemplated herein is therefore exemplified in that it comprises at least one compound of the formula (I) in which $R^1$ is $H_3C$—$(CH_2)_{15}$— or $H_3C$—$(CH_2)_{17}$— and $R^2$ is $H_3C$—$(CH_2)_{15}$— or $H_3C$—$(CH_2)_{17}$—. Such compounds are known under the INCI designation Bis-Cetearyl Amodimethicone, which is commercially available for example under the trade name Silsoft AX from the company Momentive. Accordingly, a further alkalizing component particularly preferred as contemplated herein is exemplified in that it comprises, by weight, bis-cearyl amodimethicone in a total amount of 0.1 to 2 wt. %, particularly preferably in a total amount of 0.7 to 1.5 wt. %, exceptionally preferably in a total amount of 0.9 to 1.1 wt. %.

Accordingly, a particularly preferred alkalizing component as contemplated herein is exemplified in that it comprises at least one compound of the formula (Ia), (Ib) and/or (Ic),

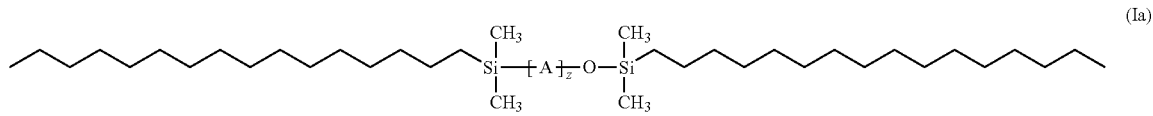

(Ia)

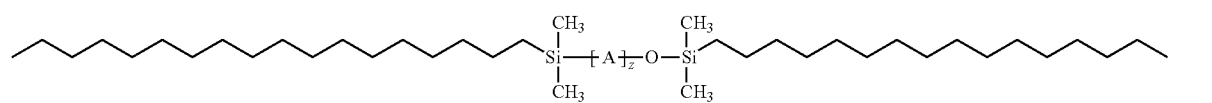

(Ib)

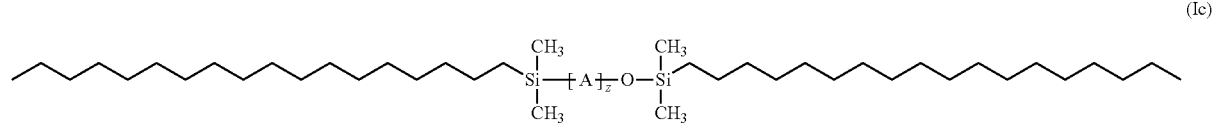

(Ic)

where the structural unit (A) in the formulae (Ia), (Ib), (Ic) each independently of one another is

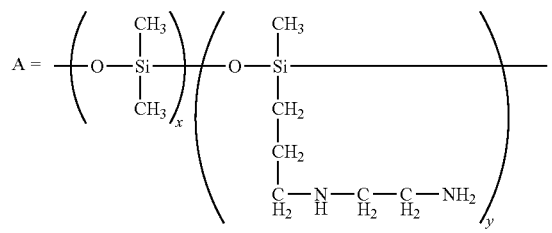

wherein
x and y independently of each other stand for values between 1 and 100,
Z stands for values between 1 and 100, whereby, if z≥is 2, the respective values x and y in a structural element A can each be selected independently of preceding structural elements A.

A further particularly preferred alkalizing component is exemplified in that it comprises, in each case by weight, at least one compound of the formula (Ia), (Ib) and/or (Ic) in a total amount of from 0.1 to 2 wt. %, particularly preferably in a total amount of from 0.7 to 1.5 wt. %, exceptionally preferably in a total amount of from 0.9 to 1.1 wt. %.

A further aminated silicone preferred as contemplated herein is selected from at least one compound of structural formula (II),

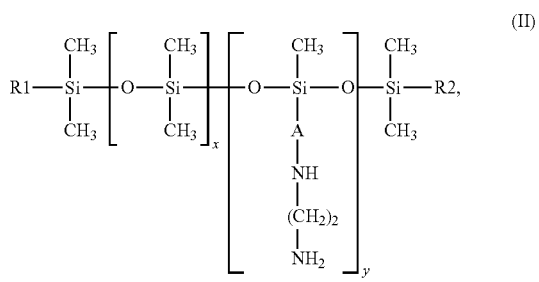

wherein
i. x and y independently of one another stand for numbers from 1 to 5000, where x preferably stands for numbers from 10 to 1800 and particularly preferably 100 to 1000, where y preferably stands for numbers from 1 to 80,
ii. R1 and R2 independently represent a methyl group or a hydroxy group, and
iii. A represents a linear or branched alkylene group with 2 to 8, preferably 3-6 and particularly preferably 3 or 4 carbon atoms, preferably a linear propylene group —CH$_2$—CH$_2$—CH$_2$— or a branched isobutylene group —CH$_2$—CH(CH$_3$)—CH$_2$.

A further alkalizing component particularly preferred as contemplated herein is exemplified in that it comprises, in each case based on its weight, at least one aminated silicone of the structural formula (II) in a total amount of 0.1 to 2 wt. %, particularly preferably in a total amount of 0.7 to 1.5 wt. %, exceptionally preferably in a total amount of 0.9 to 1.1 wt. %.

Another aminated silicone preferred by the present disclosure is selected from at least one linear copolymer comprising blocks of polydimethylsiloxane units and blocks of polyethylene glycol bis(2-methyl-2-propen-1-yl) ether monomers having the following structure (III)

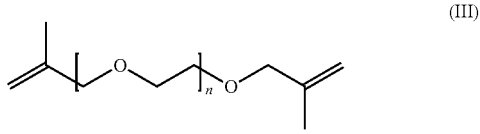

where n=14 and which is terminated with 3-{3-[bis(2-hydroxypropyl)amino]-2-hydroxypropoxy]propyl groups. A preferred linear copolymer of this type has the INCI designation Bis-Diisopropanolamino-PG-Propyl-Dimethicone 1 Bis-Isobutyl PEG-14 Copolymer. This linear copolymer is available in emulsified form under the trade designation DC CE-8411 Smooth Plus Emulsion from Dow Corning.

Alkalizing components preferred as contemplated herein are exemplified in that they comprise at least one aminated silicone selected from compounds of the structural formula (I), compounds of the structural formula (II), linear copolymers comprising blocks of polydimethylsiloxane units and blocks of polyethylene glycol-bis(2-methyl-2-propen-1-yl) ether monomers of the following structure (III)

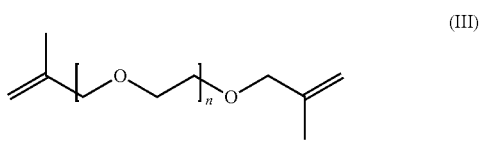

where n=14 and which are terminated with 3-{3-[bis(2-hydroxypropyl)amino]-2-hydroxypropoxy ]propyl groups, and mixtures of these compounds.

Other alkalizing components preferred as contemplated herein are exemplified in that they comprise at least one aminated silicone selected from compounds of the structural formula (I), compounds of the structural formula (II), linear copolymers comprising blocks of polydimethylsiloxane units and blocks of polyethylene glycol-bis(2-methyl-2-propen-1-yl) ether monomers of the following structure (III)

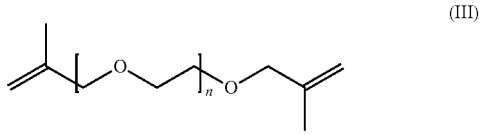

with n=14 and which are terminated with 3-{3-[bis(2-hydroxypropyl)amino]-2-hydroxypropoxy]propyl groups, and mixtures of these compounds, in a total amount of 0.1-2 wt. %, preferably 0.7-1.5 wt. %, particularly preferably 0.9 to 1.1 wt. %, in each case based on the weight of the alkalizing component.

Alkalizing components preferred as contemplated herein are exemplified by the fact that they do not contain 1,2-propylene glycol. During the development work on the present disclosure, it was found that 1,2-propylene glycol can negatively affect the skin compatibility of the colorant.

Another object of the present disclosure is a packaging unit (kit-of-parts) comprising—packaged separately from each other—.

at least one container (C1) containing an alkalizing component (M1) as contemplated herein or preferred as contemplated herein, and at least one container (C2) containing an oxidant preparation (M2) which comprises 40-96 wt. %, preferably 68-93 wt. %, particularly preferably 72-85 wt. %, of water, further hydrogen peroxide in a total amount of 0.5 to 23 wt. %, further preferably 2.5 to 21 wt. %, particularly preferably 4 to 20 wt.-%, very particularly preferably 5 to 18 wt. % and exceptionally preferably 6 to 12 wt. %, and has a pH value in the range of 2.0 to 6.5, preferably 2.5-5.5, particularly preferably 2.8 to 5.0, in each case measured at 20° C., wherein the wt. % data for (M2) relate in each case to the weight of the oxidant preparation (M2), and the oxidant preparation (M2) not containing a polymer or copolymer with acrylate-, methacrylate- or vinyl-containing monomers and not containing a polyurethane.

As contemplated herein, preferred two-part dyeing kits comprising the abovementioned components (M1) and (M2) are composed with respect to the weight ratio (M1):(M2) of the two components to one another such that the weight ratio (M1):(M2) is in the range from 1:0.8 to 1:2.5, preferably 1:1 to 1:2.

What has been said above and below for the preferred embodiments of the agent (M1) as contemplated herein and the agent (M2) used as contemplated herein applies mutatis mutandis to the coloring kits as contemplated herein and preferred as contemplated herein.

Another subject of the present disclosure is a method for oxidative hair dyeing comprising the following process steps:

i) providing an alkalizing component (M1) as contemplated herein or preferred as contemplated herein, and ii) Providing an oxidant preparation (M2) containing 40-96 wt. %, preferably 68-93 wt. %, particularly preferably 72-85 wt. %, of water, further containing hydrogen peroxide in a total amount of 0.5 to 23 wt. %, further preferably 2.5 to 21 wt. %, particularly preferably 4 to 20 wt. %, most preferably 5 to 18 wt. % and exceptionally preferably 6 to 12 wt.-%, and having a pH in the range from 2.0 to 6.5, preferably 2.5-5.5, particularly preferably 2.8 to 5.0, in each case measured at 20° C., the wt. % data in each case being based on the weight of the oxidant preparation (M2), the oxidant preparation (M2) containing no polymer or copolymer with acrylate-, methacrylate- or vinyl-containing monomers and no polyurethane, iii) Mixing the alkalizing component (M1) with the oxidizing agent preparation (M2), preferably in a weight ratio (M1):(M2) in the range of 1:0.8 to 1:2.5, preferably 1:1 to 1:2, directly followed by iv) Apply the mixture obtained in step iii) to the hair and leave this mixture on the hair for a time of 1 to 60 minutes, preferably of 20 to 45 minutes, at room temperature and/or at 30-60° ° C., preferably at 32-50° C., v) rinsing the hair with water and/or a cleansing composition, and vi) if necessary, apply an after-treatment agent to the hair and rinse if necessary, followed by drying.

For oxidative hair dyeing processes, the alkalizing component (M1) as contemplated herein is usually mixed with an aqueous oxidant-containing composition (M2) to form the ready-to-use hair dye immediately before application to the hair, and then applied to the hair. In most cases, the alkalizing component (M1) as contemplated herein and the oxidizing agent-containing composition (M2) are matched to each other in such a way that, at a mixing ratio of 1 to 1, based on parts by weight, there is an initial concentration of hydrogen peroxide of 0.5-12 wt. %, preferably 2-10 wt. %, particularly preferably 3-6 wt. % hydrogen peroxide (calculated as 100% $H_2O_2$), in each case based on the weight of the application mixture, in the finished application mixture. However, it is just as well possible to match the alkalizing component (M1) as contemplated herein and the oxidizing agent-containing composition (M2) to each other in such a way that the concentrations required in the ready-to-use colorant (application mixture) result from mixing ratios other than 1:1, for example by a weight-related mixing ratio of 1:2 or 1:3 or even 2:3.

As contemplated herein, preferred weight-related mixing ratios (M1):(M2) are in the range from 1:0.8 to 1:2.5, particularly preferred in the range from 1:1 to 1:2.

As contemplated herein, the term "Room temperature" denotes the temperature in the room in which a person usually uses a hair dye, that is to say usually a bathroom or a hairdressing salon, where a temperature in the range from 10-29° C. prevails.

Leaving the hair coloring application mixture in process step iv) in the hair coloring processes as contemplated herein or preferred as contemplated herein can also take place at min 30° C., preferably at 30-60° C., particularly preferably at 32-50° C., if the hair is heated, for example, with a heat hood or a radiant heater.

The oxidizing agent preparation (M2) used in dyeing kits as contemplated herein and in dyeing processes preferred as contemplated herein comprises, in each case based on its weight, 40-96 wt. %, preferably 68-93 wt. %, particularly preferably 72-85 wt. %, of water. The oxidizing agent preparation (M2) used in dyeing kits as contemplated herein and in dyeing processes preferred as contemplated herein further comprises, in each case based on its weight, 0.5-23 wt. %, further preferred 2.5-21 wt. %, particularly preferred 4-20 wt. %, very particularly preferred 5-18 wt. % and exceptionally preferred 6-12 wt. %, of hydrogen peroxide.

To stabilize the hydrogen peroxide, the oxidizer preparation (M2) has a pH in the range from 2.0 to 6.5, preferably 2.5-5.5, particularly preferably 2.8 to 5.0, in each case measured at 20° C. The oxidant preparation (M2) does not contain any polymer or copolymer with acrylate-, methacrylate- or vinyl-containing monomers and no polyurethane.

Hair dyes which are ready for use as contemplated herein and include an alkalizing component (M1) preferred as contemplated herein or as contemplated herein and an oxidizing agent preparation (M2) are exemplified in that they have a viscosity in the range from 5,000 to 45,000 mPa-s, preferably from 10,000 to 35,000 mPa-s, particularly preferably from 15,000 to 30,000 mPa-s, in each case measured at 20° C. These viscosities are excellent for the handling of this agent itself (preparation, spread ability on the hair, residence behavior during the application time). The parameters for the viscosity measurements are: Device: Brookfield viscometer RDV-II+: temperature: 20° C.: spindle 5: shear rate: 4 revolutions per minute (4 RPM).

The oxidizing agent preparation (M2) used in hair dyeing kits preferred as contemplated herein and in hair dyeing processes preferred as contemplated herein comprises at least one surfactant selected from anionic surfactants and nonionic surfactants and mixtures thereof in a total amount of 0.05-2 wt. %, preferably 0.3-1.5 wt.-%, and at least one linear saturated 1-alkanol having 14 to 22 carbon atoms selected from 1-tetradecanol (myristyl alcohol), 1-hexadecanol (cetyl alcohol), 1-octadecanol (stearyl alcohol) and 1-eicosanol (arachyl alcohol) and mixtures thereof, in a total amount of 1-5 wt. %, preferably 1.5-4 wt. %, all amounts being based on the weight of the oxidant preparation (M2).

For the purposes of the present application, the aforementioned linear, saturated 1-alkanols with a hydroxyl group are not counted as surfactants.

The anionic surfactants used in the oxidizing agent preparations (M2) used as contemplated herein are selected from the same anionic surfactants from which the anionic surfactants included in the agents (M1) used as contemplated herein are selected.

Particularly preferred nonionic surfactants for the oxidant preparations (M2) used as contemplated herein are selected from castor oil ethoxylated with 7-80 mol ethylene oxide per mol, ethoxylated $C_8$-$C_{24}$ alkanols with 5-30 mol ethylene oxide per mol, ethoxylated $C_8$-$C_{24}$ carboxylic acids with 5-30 mol ethylene oxide per mol, sorbitan monoesters of linear saturated and unsaturated $C_{12}$-$C_{30}$ carboxylic acids which may be hydroxylated, in particular those of myristic acid, palmitic acid, stearic acid or of mixtures of these fatty acids, alkyl mono- and oligoglycosides containing 8 to 22 carbon atoms in the alkyl radical and their ethoxylated analogues, and mixtures of the abovementioned substances, ethoxylated with 4-50 mol ethylene oxide per mol.

The ethoxylated $C_8$-$C_{24}$-Alkanols have the formula $R^1O(CH_2CH_2O)_nH$, where $R^1$ stands for a linear or branched alkyl and/or alkenyl radical with 8-24 carbon atoms and n, the average number of ethylene oxide units per molecule, for numbers from 5-30, preferably 6-20, particularly preferably 6 to 12 moles of ethylene oxide to 1 mole of alkanol, which is preferably selected from caprylic alcohol, 2-Ethylhexyl alcohol, capric alcohol, lauryl alcohol, isotridecyl alcohol, tridecyl alcohol, myristyl alcohol, cetyl alcohol, palmitoleyl alcohol, stearyl alcohol, isost, Oleyl alcohol, elaidyl alcohol, petroselinyl alcohol, arachyl alcohol, gadoleyl alcohol, behenyl alcohol, erucyl alcohol and brassidyl alcohol and from their technical mixtures. Adducts of 10-100 moles of ethylene oxide to technical fatty alcohols with 12-18 carbon atoms, such as coconut, palm, palm kernel or tallow fatty alcohols, are also suitable. Particularly preferred are trideceth-6, isotrideceth-6, undeceth-6, myreth-6, laureth-10, laureth-12, laureth-15, laureth-20, laureth-30, myreth-10, myreth-12, myreth-15, myreth-20, myreth-30, ceteth-10, ceteth-12, ceteth-15, ceteth-20, ceteth-30, steareth-10, Steareth-12, Steareth-15, Steareth-20, Steareth-30, Oleth-10, Oleth-12, Oleth-15, Oleth-20, Oleth-30, Ceteareth-10, Ceteareth-15, Ceteareth-12, Ceteareth-15, Ceteareth-20, Ceteareth-30, and Coceth-10, Coceth-12, Coceth-15, Coceth-20 and Coceth-30; exceptionally preferred are castor oil ethoxylates, in particular PEG-40 castor oil, and ethoxylated fatty alcohols, in particular Ceteth-20 and Steareth-20, as well as mixtures of castor oil ethoxylates and ethoxylated fatty alcohols, in particular mixtures of PEG-40 castor oil, Ceteth-20 and Steareth-20.

Oxidant preparations (M2) preferred as contemplated herein contain at least one nonionic surfactants in a total amount of 0.5-2.5 wt. %, preferably 1.0 to 1.6 wt. %, in each case based on the weight of (M2). Oxidant preparations (M2) preferred as contemplated herein contain at least one nonionic surfactant selected from castor oil ethoxylates, in particular PEG-40 castor oil, and ethoxylated fatty alcohols, in particular ceteth-20 and steareth-20, and mixtures thereof, in a total amount of 0.5-2.5 wt. %, preferably 1.0 to 1.6 wt. %, in each case based on the weight of (M2).

In a further preferred embodiment of the present disclosure, the oxidant preparation (M2) used as contemplated herein comprises at least one oil in a total amount of 0.2-50 wt. %, preferably 2-40 wt. %, particularly preferably 5-30 wt. %, exceptionally preferably from 10-12 wt. %, in each case based on the weight of the oxidant preparation (M2).

The at least one oil included in the oxidant preparation (M2) in a total amount of 0.2-50 wt. %, preferably 2-40 wt. %, particularly preferably 5-30 wt. %, exceptionally preferably 10-12 wt. %, in each case based on the weight of the preparation (M2), is preferably selected from natural and synthetic hydrocarbons, particularly preferably from mineral oil, kerosene oils, $C_{18}$-$C_{30}$ isoparaffins, especially isoeicosane, polyisobutenes and polydecenes, $C_8$-$C_{16}$ isoparaffins, and 1,3-di-(2-ethylhexyl)-cyclohexane: the benzoic acid esters of linear or branched $C_{8-22}$ alkanols: triglycerides of linear or branched, saturated or unsaturated, optionally hydroxylated $C_{8-30}$ fatty acids, in particular natural oils: the dicarboxylic acid esters of linear or branched $C_2$-C10 alkanols: the esters of linear or branched saturated or unsaturated fatty alcohols with 2-30 carbon atoms with linear or branched saturated or unsaturated fatty acids with 2-30 carbon atoms, which may be hydroxylated: branched fatty alcohols: the $C_8$-$C_{22}$ fatty alcohol esters of monovalent or polyvalent $C_2$-$C_7$ hydroxycarboxylic acids: the symmetrical, asymmetrical or cyclic esters of carbonic acid with $C_{3-22}$ alkanols, $C_{3-22}$ alkanediols or $C_{3-22}$ alkanetriols, and mixtures of the above mentioned substances. In this context, particularly preferred oils as contemplated herein are selected from at least one ester of linear or branched saturated or unsaturated fatty alcohols having 2-30 carbon atoms with linear or branched saturated or unsaturated fatty acids having 2-30 carbon atoms, which may be hydroxylated, and mixtures thereof: exceptionally preferably selected from isopropyl palmitate and isopropyl myristate and mixtures thereof.

Cationic Surfactant in the Oxidant Preparation (M2)

The above viscosity of agents (M1) preferred as contemplated herein is excellent for handling this agent itself (preparation, filling, dosing to prepare the mixture with the oxidant preparation). The oxidant preparation (M2) usually has a low viscosity in the range of 10-6000 mPas, preferably 200-5000 mPas, especially preferably 1000-4500 mPas, each measured at 20° C. For application to the hair, however, the application mixture should have a significantly higher viscosity so that it remains on the hair during the entire application time (in the range of 5-60 minutes, preferably 30-45 minutes) and does not drip down. A distinction is made here as to whether the application mixture is produced by shaking both compositions (M1) and (M2) and, if applicable, (M3) in an application bottle, from which the application mixture is applied to the hair immediately after mixing using an application spout as a bottle attachment (bottle application), or whether the application mixture is prepared by stirring the two compositions (M1) and (M2) and, if applicable, (M3) in a bowl, from which the application mixture is applied to the hair with a brush immediately after mixing (brush application). The bottle application is particularly suitable for colorants that are sold in retail outlets with a recommendation for use by the consumer himself. Brush application is particularly suitable for colorants that are prepared in the hairdressing salon by the hairdresser and applied to the consumer's hair.

Surprisingly, it was found that an application mixture with a viscosity particularly suitable for brush application is obtained by mixing the agent (M1) according to or preferred present disclosure with an oxidizing agent preparation (M2) containing at least one cationic surfactant. Upon mixing, the interaction between the at least one anion surfactant and the at least one cation surfactant results in the desired increase in viscosity. The resulting paste-like consistency of the application mixture leads to optimal application properties, especially for brush application.

In a further preferred embodiment of the present disclosure, the oxidant preparation (M2) used as contemplated herein comprises at least one cationic surfactant, preferably in a total amount of 0.05-3% by weight, particularly preferably of 0.1-1.5% by weight, extremely preferably of 0.3-0.9% by weight, in each case based on the weight of the oxidant preparation (M2).

Cationic surfactants are surfactants, i.e. surface-active compounds, each with one or more positive charges. Cationic surfactants contain only positive charges. Usually these surfactants are composed of a hydrophobic part and a hydrophilic head group, the hydrophobic part usually comprising a hydrocarbon backbone (e.g. comprising one or two linear or branched alkyl chains) and the positive charge(s) being located in the hydrophilic head group. Cationic surfactants adsorb at interfaces and aggregate in aqueous solution above the critical micelle formation concentration to form positively charged micelles.

As contemplated herein, cationic surfactants of the type of quaternary ammonium compounds, esterquats and alkylamidoamines are preferred. Preferred quaternary ammonium compounds are ammonium halides, such as alkyltrimethylammonium chlorides, dialkyldimethylammonium chlorides, trialkylmethylammonium chlorides, as well as the imidazolium compounds known under the INCI designations Quaternium-27 and Quaternium-83. Other preferred quaternary ammonium compounds are tetraalkylammonium salts, such as in particular the quaternium-52 known under the INCI designation, a poly (oxy-1,2-ethanediyl), ((octadecylnitrilio)tri-2, 1-ethanediyl)tris(hydroxy)phosphate (1:1) salt, which has the general structural formula (III), wherein x+y+z=10:

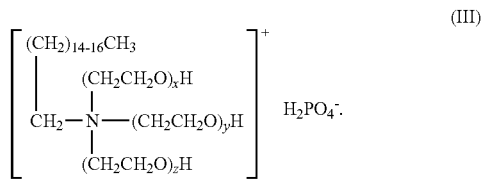

The long alkyl chains of the surfactants mentioned above preferably have 10 to 22, particularly preferably 12 to 18 carbon atoms. Behenyl trimethylammonium chloride, stearyl trimethylammonium chloride and cetyl trimethylammonium chloride are particularly preferred, with stearyl trimethylammonium chloride being extremely preferred. Further cationic surfactants suitable as contemplated herein are quaternized protein hydrolysates. Alkylamidoamines are usually produced by amidation of natural or synthetic fatty acids and fatty acid cuts with dialkylaminoamines. Tegoamid® S 18 (stearamidopropyldimethylamine) is a suitable compound from this group of substances. Esterquats are substances which contain both at least one ester function and at least one quaternary ammonium group as a structural element. Preferred esterquats are quaternized ester salts of fatty acids with triethanolamine, quaternized ester salts of fatty acids with diethanolalkylamines and quaternized ester salts of fatty acids with 1,2-dihydroxypropyl dialkylamines.

In terms of optimum application properties and optimal dyeing results, C10-C22 alkyltrimethylammonium chlorides have proven to be particularly suitable. Particularly preferred oxidizing agent preparations (M2) used as contemplated herein are therefore exemplified in that they are extremely preferred at least one cationic surfactant in a total amount of 0.05-3% by weight, particularly preferably 0.1-1.5% by weight from 0.3 to 0.9% by weight, based in each case on the weight of the oxidizing agent preparation (M2), preferably at least one surfactant selected from C10-C22-alkyltrimethylammonium chlorides, in particular selected from behenyltrimethylammonium chloride, stearyltrimethylammonium chloride and cetyltrimethylammonium chloride, and mixtures of these surfactants. Extremely preferred oxidant preparations (M2) used as contemplated herein contain stearyl trimethylammonium chloride in a total amount of 0.05-3 wt. %, particularly preferably 0.1-1.5 wt. %, extremely preferably 0.3-0.9 wt. %, each based on the weight of the oxidant preparation (M2).

A further packaging unit (kit-of-parts) preferred as contemplated herein and a further dyeing process preferred as contemplated herein are each exemplified in that the oxidant preparation (M2) comprises at least one cationic surfactant, preferably in a total amount of 0.05-3 wt. %, particularly preferably of 0.1-1.5 wt. %, exceptionally preferably of 0.3-0.9 wt. %, in each case based on the weight of the oxidant preparation (M2).

A further kit-of-parts preferred as contemplated herein and a further dyeing method preferred as contemplated herein are each exemplified in that the oxidant preparation (M2) comprises at least one surfactant selected from anionic surfactants and nonionic surfactants and mixtures thereof in a total amount of 0.05-2 wt. %, preferably 0.3-1.5 wt. %, and at least one linear, saturated 1-alkanol having 14 to 22 carbon atoms, selected from 1-tetradecanol (myristyl alcohol), 1-hexadecanol (cetyl alcohol), 1-octadecanol (stearyl alcohol) and 1-eicosanol (arachyl alcohol) and mixtures thereof, in a total amount of 1-5 wt. %, preferably 1.5-4 wt. %, in each case based on the weight of the oxidant preparation (M2).

A further kit-of-parts preferred as contemplated herein and a further dyeing process preferred as contemplated herein are each exemplified in that the oxidant preparation (M2) comprises at least one surfactant selected from anionic surfactants and nonionic surfactants and mixtures thereof in a total amount of 0.05-2 wt. %, preferably 0.3-1.5 wt. %, at least one linear, saturated 1-alkanol having 14 to 22 carbon atoms, selected from 1-tetradecanol (myristyl alcohol), 1-hexadecanol (cetyl alcohol), 1-octadecanol (stearyl alcohol) and 1-eicosanol (arachyl alcohol), as well as mixtures thereof, in a total amount of 1-5 wt.-%, preferably 1.5-1.5 wt.-%, preferably 1.5-1.5 wt.-%, and mixtures thereof. %, preferably 1.5-4 wt. %, and at least one oil in a total amount of 0.2-50 wt. %, preferably 2-40 wt. %, particularly preferably 5-30 wt. %, exceptionally preferably 10-12 wt. %, in each case based on the weight of the oxidant preparation (M2).

The oxidizing agent preparations (M2) used as contemplated herein and preferably used as contemplated herein may also contain stabilizers, especially complexing agents, and pH buffer substances.

With respect to the cosmetic agent (M1) in container C1 and the oxidizing agent preparation (M2) in container C2 of the preferred kits, what has been said about the Preferred Cosmetics applies mutatis mutandis.

With regard to the cosmetic agent (M1) in container C1 of the processes for oxidative hair coloring as contemplated herein and preferred as contemplated herein, what has been said about the cosmetic agents as contemplated herein and preferred as contemplated herein applies mutatis mutandis.

With regard to the oxidizing agent preparation (M2) in container C2 of the oxidative hair dyeing processes as contemplated herein and preferred as contemplated herein, the same applies mutatis mutandis as to the oxidizing agent preparations (M2) of the oxidative hair dyeing kits as contemplated herein and preferred as contemplated herein.

The walls of containers C1 and C2 are preferably made of a polyolefin, such as polypropylene (PP), high density polyethylene (HDPE), medium density polyethylene (MDPE), low density polyethylene (LDPE), linear low density polyethylene (LLDPE). Among these, polyethylene, especially high density polyethylene (HDPE), is preferred.

For improved mixing of (M1) and (M2), it is preferred that the container (C2) containing the oxidant preparation (M2) is designed as a bottle and has a reclosable opening, such as a snap-on or screw cap. This makes it easier to add the color-changing agent from container (C1), which in turn is preferably in the form of a polyolefin bottle.

The following examples are intended to illustrate the subject matter of the present disclosure, without restricting it thereto.

Experimental Part

The following alkalizing component (M1) and oxidizing agent preparation (M2) were prepared by mixing the tabulated ingredients together (all amounts in wt. %):

TABLE 1

Alkalizing component (M1)
all quantities in wt. %

| | |
|---|---|
| Xanthan gum | 1.5000 |
| Cellulose Gum (Carboxymethyl-cellulose, Sodium Salt) | 0.9000 |
| 2-Octyldodecanol | 4.5200 |
| Ammonium hydroxide ($NH_4OH$) | 3.9000 |
| Ammonium sulfate (($NH_4)_2SO_4$) | 0.5000 |
| Potassium hydroxide | 0.1500 |
| Etidronic acid | 0.1200 |
| Sodium laureth sulfate (2 EO) | 0.8100 |
| Bis-Cetearyl Amodimethicone | 1.0000 |
| Sodium Gluceptate (Sodium Heptagluconate) | 0.9000 |
| Sodium sulfite | 0.5000 |
| Ascorbic acid | 0.4000 |
| Toluene-2,5-diamine sulfate | 0.0800 |
| 3-methyl-4-aminophenol | 0.0200 |
| Resorcinol | 0.0520 |
| m-Aminophenol | 0.0050 |
| 1,3-Bis-(2,4-diamino-phenoxy)propane HCl | 0.0015 |
| Perfume | 0.4000 |
| Water, demineralized (Aqua) | 84.2415 |
| | 100,0000 |

Viscosity: 81,700 mPas (Brookfield viscometer RDV-II+; 20° C.; spindle 5; 4 RPM) pH value: 10,36 (20° C.)

TABLE 2

Oxidizer preparation (M2)
all quantities in wt. %

| | |
|---|---|
| Hydrogen peroxide | 11.500 |
| Isopropyl myristate | 10.000 |
| Cetearyl alcohol | 3.600 |
| PEG-40 Castor Oil | 0.600 |
| Ceteareth-20 | 0.500 |
| Sodium cetaryl sulfate | 0.300 |
| Etidronic acid | 0.240 |
| Potassium hydroxide | 0.137 |
| 2,6-Dicarboxypyridine | 0.100 |

TABLE 2-continued

Oxidizer preparation (M2)
all quantities in wt. %

| | |
|---|---|
| Disodium pyrophosphate | 0.100 |
| Sodium sulfate | 0.0130 |
| Water, demineralized (Aqua) | 72.910 |
| | 100,000 |

Preparation of the Hair Dye Ready for Use

The alkalizing component according to Table 1 was mixed with the oxidizing agent preparation (M2) according to Table 2 in the mixing ratio 60:60 by weight ((M1):(M2)).

The obtained ready-to-use hair dye has the following properties:

Viscosity: 21,600 mPas (Brookfield viscometer RDV-II+; 20° C.; spindle 5; 4 RPM)

pH value: 9,67)(20° ° C.

Application:

The ready-to-use hair dye was applied to the dry hair to be dyed and rinsed with water after an exposure time of 30-45 minutes. The hair was still cleaned with a shampoo, if desired, washed out again, retreated with a conditioner, washed out again, dried with a towel and then blow-dried at 35-80° C.

With the hair dye No. 1 as contemplated herein, a lightening coloration of the hair was achieved.

Improvement of the Consistency and Spread Ability of the Application Mixture on the Hair Due to the Alkalizing Component as Contemplated Herein.

TABLE 3

Alkalizing component (M1)
all quantities in wt. %

| | (M1)-E (see Tab. 1) | (M1)-comparison |
|---|---|---|
| Xanthan gum | 1.500 | 0.000 |
| Cellulose Gum (Carboxymethyl-cellulose, Sodium Salt) | 0.900 | 0.000 |
| Cetearyl alcohol | 0.0000 | 5.7500 |
| Coconut fatty alcohol | 0.0000 | 2.7000 |
| 2-Octyldodecanol | 4.5200 | 0.0000 |
| Ammonium hydroxide ($NH_4OH$) | 3.9000 | 3.9000 |
| Ammonium sulfate (($NH_4)_2SO_4$) | 0.5000 | 0.5000 |
| Potassium hydroxide | 0.1500 | 0.6500 |
| Etidronic acid | 0.1200 | 0.1200 |
| Sodium laureth sulfate (2 EO) | 0.8100 | 1.6200 |
| Ceteareth-20 | 0.0000 | 0.2500 |
| Bis-Cetearyl Amodimethicone | 1.0000 | 1.0000 |
| Sodium Gluceptate (Sodium Heptagluconate) | 0.9000 | 0.0000 |
| Sodium sulfite | 0.5000 | 0.5000 |
| Ascorbic acid | 0.4000 | 0.4000 |
| Toluene-2,5-diamine sulfate | 0.0800 | 0.0800 |
| 3-methyl-4-aminophenol | 0.0200 | 0.0200 |
| Resorcinol | 0.0520 | 0.0520 |
| m-Aminophenol | 0.0050 | 0.0050 |
| 1,3-Bis-(2,4-diamino-phenoxy)propane HCl | 0.0015 | 0.0015 |
| Perfume | 0.4000 | 0.4000 |
| Water, demineralized (Aqua) | 84.2415 | 82.0515 |
| | 100,000 | 100,0000 |

Hair Dyeing Composition as Contemplated Herein:

The alkalizing component according to Table 1 was mixed with the oxidizing agent preparation (M2) according to Table 2 in a mixing ratio of 60:60 by weight.

Comparative Hair Dye (not as Contemplated Herein):

The alkalizing component not as contemplated herein as shown in Table 3 was mixed with the oxidizing agent preparation (M2) as shown in Table 2 in a mixing ratio of 60:60 by weight.

Application:

The ready-to-use hair dyes according to Table 3 (as contemplated herein and not as contemplated herein) were each applied to dry hair in 3 test subjects.

The exposure time to the hair in the attachment area was 40 minutes.

The exposure time to the hair in the length area was 5 minutes.

After the exposure time, the hair dye was rinsed out of the hair with water. The hair was towel dried and then blow dried at 40° C.

The assessment was made by trained hairdressers for each criterion mentioned in Table 4 below on a grading scale of 1 to 6, where 1 means "poor" and 6 means "excellent".

TABLE 4

Test results for the hair dye as contemplated herein

| | Hair dye (as contemplated herein) | Test person | | | Arithmetic mean |
|---|---|---|---|---|---|
| | | 1 | 2 | 3 | |
| Assessment after application | Simplicity of mixing | 5 | 5 | 5 | 5.00 |
| | Skin irritation (before application) | 5 | 5 | 5 | 5.00 |
| | Skin irritation (after application) | 5 | 5 | 5 | 5.00 |
| | Consistency of the application mixture | 5 | 5 | 5 | 5.00 |
| | Simplicity of the application | 5 | 5 | 5 | 5.00 |
| | Hair feel of the dry hair | 5 | 5 | 5 | 5.00 |
| | Color depth achieved | 5 | 5 | 5 | 5.00 |
| | Achieved color direction | 5 | 5 | 5 | 5.00 |
| | Uniformity of coloring | 5 | 5 | 5 | 5.00 |
| | Gloss | 5 | 5 | 5 | 5.00 |
| | Scalp feeling | 5 | 5 | 5 | 5.00 |
| | Conclusion | OK | OK | OK | |

TABLE 5

Test results for the hair dyeing composition not as contemplated herein

| | Hair dye (comparison, not as contemplated herein) | Test person | | | Arithmetic mean |
|---|---|---|---|---|---|
| | | 1 | 2 | 3 | |
| Assessment after application | Simplicity of mixing | 5 | 5 | 5 | 5.00 |
| | Skin irritation (before application) | 5 | 5 | 5 | 5.00 |
| | Skin irritation (after application) | 5 | 5 | 5 | 5.00 |
| | Consistency of the application mixture | 5 | 4 | 5 | 4.67 |
| | Simplicity of the application | 5 | 4 | 5 | 4.67 |
| | Hair feel of the dry hair | 5 | 5 | 5 | 5.00 |
| | achieved whitening | 5 | 5 | 5 | 5.00 |
| | Achieved color direction | 5 | 5 | 5 | 5.00 |
| | Uniformity of coloring | 5 | 5 | 5 | 5.00 |
| | Gloss | 5 | 5 | 5 | 5.00 |
| | Scalp feeling | 5 | 5 | 5 | 5.00 |
| | Conclusion | OK | OK | OK | |

With the alkalizing component as contemplated herein, better spread ability on the hair is achieved than with the comparative composition.

The improved spread ability of the application mixture with the alkalizing component as contemplated herein on the hair can also be demonstrated by applying both application mixtures (with the alkalizing component as contemplated herein or with the comparative alkalizing component (M1)) to a glass plate and placing it at a slight angle. The comparison application mixture slides down the plate in a while the application mixture with the alkalizing component as contemplated herein spreads over the plate.

TABLE 6

Further alkalizing components as contemplated herein (M1) all quantities in wt. %

| | 6.1 | 6.2 |
|---|---|---|
| Xanthan gum | 1.500 | 1.500 |
| Cellulose Gum (Carboxymethylcellulose, Sodium Salt) | 0.900 | 0.900 |
| 2-Octyldodecanol | 4.520 | 4.520 |
| Ammonium hydroxide ($NH_4OH$) | 4.000 | 3.340 |
| Monoethanolamine (2-aminoethanol) | 3.600 | 0.000 |
| Ammonium sulfate (($NH_4$)$_2SO_4$) | 0.500 | 0.900 |
| Sodium hydroxide | 0.045 | 0.045 |
| Etidronic acid | 0.120 | 0.120 |
| Sodium laureth sulfate (2 EO) | 0.810 | 0.810 |
| Bis-Cetearyl Amodimethicone | 1.000 | 1.000 |
| Sodium Gluceptate (Sodium Heptagluconate) | 0.900 | 0.900 |
| Sodium sulfite | 0.400 | 0.400 |
| Ascorbic acid | 0.100 | 0.100 |
| Toluene-2,5-diamine sulfate | 0.039 | 0.0095 |
| 1-Hydroxyethyl-4,5-diaminopyrazole sulfate | 0.024 | 0.000 |
| 2-methylresorcinol | 0.0197 | 0.0000 |
| Resorcinol | 0.0088 | 0.0520 |
| m-Aminophenol | 0.0009 | 0.0050 |
| 1,3-Bis-(2,4-diaminophenoxy)propane HCl | 0.0098 | 0.0015 |
| 2,4-Diaminophenoxyethanol HCl | 0.0064 | 0.0000 |
| 4-Amino-2-methylphenol | 0.0040 | 0.0000 |
| 4-Amino-2-hydroxytoluene | 0.0011 | 0.0000 |
| 2-Amino-4-hydroxyethyl-aminoanisole sulfate | 0.0000 | 0.0121 |
| Perfume | 0.4000 | 0.4000 |
| Water, demineralized (Aqua) | 81.0913 | 84.9849 |
| | 100,000 | 100,000 |
| pH value (20° C.) | 10.0-11.0 | 10.0-11.0 |

Hair Dyeing Compositions as Contemplated Herein:

The alkalizing component according to Table 6 (Example 6.1 or Example 6.2) was mixed with the oxidizer preparation (M2) according to Table 2 in a mixing ratio of 60:60 by weight.

This application mixture was applied to dry hair. The exposure time to the hair in the attachment area was 40 minutes. The exposure time to the hair in the length area was 15 minutes. After the exposure time, the hair dye was rinsed out of the hair with water. The hair was dried with a towel and then blow-dried at 70° C.

Optionally, after rinsing out the hair dye, the hair can still be treated with a hair conditioner, which is rinsed out of the hair after an exposure time of 1-10 minutes. The hair is then first dried with a towel and finally blow-dried at 70° C.

Optionally, after rinsing out the hair dye, the hair can still be treated with a hair conditioner, which remains on the hair. The hair is then first dried with a towel and finally blow-dried at 70° C.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. Alkalizing component for an oxidative hair dyeing composition comprising
   about 76-about 92 wt. % water,
   about 1-about 2 wt. % xanthan gum,
   about 0.5-about 1.5 wt. % sodium carboxymethyl cellulose,
   at least one dye chosen from oxidation dye precursors and direct dyes and mixtures thereof; in a total amount of about 0.0001-about 6 wt. %,
   at least one alkalizing agent chosen from ammonium hydroxide and alkanolamines and mixtures thereof; in a total amount of about 3-about 9 wt. %,
   at least one oil in a total amount of about 0.5-about 7.0 wt. %,
   at least one surfactant chosen from anionic, zwitterionic, amphoteric and alkyl oligoglycoside surfactants substituted with at least one C8 to C14 alkyl radical, in a total amount of about 0.4-about 2 wt. %,
   about 0-about 0.1 wt. % peroxide,
   where all figures in % by weight are based on the weight of the alkalizing component,
   wherein the alkalizing component has a pH in the range of about 8.0 to about 12.0, measured at about 20° C.,
   where no percarbonate is present,
   wherein no polymer or copolymer with acrylate-, methacrylate- or vinyl-containing monomers and no polyurethane is present, and
   wherein no fat component having a melting point of about 28° C. or higher is included.

2. Alkalizing component according to claim 1, having a viscosity in the range of about 2,000 to about 110,000 mPa·s measured at about 20° C.

3. Alkalizing component according to claim 1, wherein no polysaccharide other than xanthan gum and sodium carboxymethylcellulose is present.

4. Alkalizing component according to claim 1, wherein the alkanolamine used as alkalizing agent is chosen from primary amines having a $C_2$-$C_6$ alkyl structure carrying at least one hydroxyl group.

5. An alkalizing component according to claim 1, wherein the at least one oil is chosen from branched, saturated fatty alcohols having 6-30 carbon atoms and from the esters of saturated, linear or branched fatty alcohols having 2-30 carbon atoms with saturated, linear or branched fatty acids having 2-30 carbon atoms, which may be hydroxylated, and mixtures thereof.

6. An alkalizing component according to claim 1, wherein glucoheptonic acid and/or at least one of its physiologically tolerated salts and/or lactones is further present, in a total amount of about 0.1 to about 2 wt. %, based on the weight of free glucoheptonic acid in relation to the weight of the alkalizing component.

7. Alkalizing component according to claim 1, wherein at least one aminated silicone is present, preferably in a total amount of about 0.1 to about 2 wt. % based on the weight of the alkalizing component.

8. An alkalizing component according to claim 1, wherein at least one oxidation dye precursor chosen from developer components and coupler components and mixtures thereof is included and wherein the at least one developer component is chosen from toluene-2,5-diamine, 2-methoxymethyl-p-phenylenediamine, 2-(2,5-diaminophenyl)ethanol, p-phenylenediamine, 2-(1,2-dihydroxyethyl)-p-phenylenediamine, N,N-bis-(2-hydroxyethyl)-p-phenylenediamine, 4,5-diamino-1-(2-hydroxyethyl)-1H-pyrazole, 4-aminophenol, 3-methyl-4-aminophenol, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diamino-propan-2-ol, Bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo-[1,2-a]-pyrazol-1-one and physiologically tolerated salts and mixtures thereof, in a total amount of about 0.0001-about 6 wt. % based on the weight of the alkalizing component.

9. Alkalizing component according to claim 1, wherein no oxidation dye precursor but only at least one direct dye is present, preferably in a total amount of about 0.0001-about 6 wt. % based on the weight of the alkalizing component.

10. Packing unit (kit-of-parts), comprising—packed separately from each other—
    at least one container (C1) comprising an alkalizing component according to claim 1, and
    at least one container (C2) comprising an oxidant preparation (M2) which comprises about 40-about 96 wt. % of water and comprising hydrogen peroxide in a total amount of about 0.5 to about 23 wt. %, and has a pH value in the range of about 2.0 to about 6.5 measured at about 20° C., wherein the wt. % data for (M2) relate in each case to the weight of the oxidant preparation (M2), and
    the oxidant preparation (M2) does not comprise a polymer or copolymer with acrylate-, methacrylate- or vinyl-containing monomers and does not comprise a polyurethane.

11. A process for oxidative hair dyeing comprising the following process steps:
    i) Providing an alkalizing component (M1) according to claim 1,
    ii) Providing an oxidant preparation (M2) comprising about 40-about 96 wt. % of water, and comprising hydrogen peroxide in a total amount of about 0.5 to about 23 wt. % and has a pH value in the range from about 2.0 to about 6.5 measured at 20° C., the wt. % data for (M2) relating in each case to the weight of the oxidant preparation (M2), and
    the oxidant preparation (M2) not comprising a polymer or copolymer with acrylate-, methacrylate- or vinyl-containing monomers and not comprising a polyurethane,
    iii) Mixing the alkalizing component (M1) with the oxidizing agent preparation (M2) in a weight ratio (M1):(M2) in the range of about 1:0.8 to about 1:2.5, directly followed by
    iv) applying the mixture obtained in step iii) to the hair and leaving this mixture on the hair for a time of about 1 to about 60 minutes at room temperature and/or at about 30-about 60° C.,
    v) rinsing the hair with water and/or a cleansing composition, and
    optionally applying an after-treatment agent to the hair and optionally rinsing followed by drying.

12. Alkalizing component according to claim 1 wherein the at least one oil is present in a total amount of about 2.0-about 5.5 wt. %, and wherein the alkalizing component has a pH in the range of about 9.6 to about 11.5, measured at about 20° ° C.

13. Alkalizing component according to claim 1 wherein the at least one oil is present in a total amount of about 3.5-about 5.0 wt. %, and wherein the alkalizing component has a pH in the range of about 10.0 to about 11.0, measured at about 20° C.

14. Alkalizing component according to claim 12, having a viscosity in the range of about 40,000 to about 100,000 mPa-s, measured at about 20° C.

15. Alkalizing component according to claim 12, having a viscosity in the range of about 70,000 to about 90,000 mPa-s, measured at about 20° C.

16. Alkalizing component according to claim 13, having a viscosity in the range of about 40,000 to about 100,000 mPa-s, measured at about 20° C.

17. Alkalizing component according to claim 13, having a viscosity in the range of about 70,000 to about 90,000 mPa-s, measured at about 20° C.

18. Alkalizing component according to claim 1, having a viscosity in the range of about 40,000 to about 100,000 mPa-s, measured at about 20° C.

19. Alkalizing component according to claim 1, having a viscosity in the range of about 70,000 to about 90,000 mPa-s, measured at about 20° C.

* * * * *